United States Patent [19]

Galbo

[11] Patent Number: 5,015,682
[45] Date of Patent: May 14, 1991

[54] OLIGOMERIC N-HYDROCARBYLOXY HINDERED AMINE LIGHT STABILIZERS

[75] Inventor: James P. Galbo, Hartsdale, N.Y.

[73] Assignee: Ciba-Geigy Corporation, Ardsley, N.Y.

[21] Appl. No.: 481,033

[22] Filed: Feb. 14, 1990

Related U.S. Application Data

[63] Continuation-in-part of Ser. No. 326,703, Mar. 21, 1989, abandoned.

[51] Int. Cl.[5] .............................................. C08K 5/3435
[52] U.S. Cl. .................................... 524/102; 524/103; 546/15; 546/187
[58] Field of Search ........................ 524/99, 102, 103; 546/188, 187

[56] References Cited

FOREIGN PATENT DOCUMENTS 1196444  11/1985  Canada .............................. 524/102

OTHER PUBLICATIONS

Shlyapintokh et al., "Developments in Polymer Stabilisation", V 41-70 (1982).
T. Fujita et al., J. Polym. Sci. Polymer Lett. Ed. 16, 515 (1978).
Miyazawa et al., *Synthesis* (1034).

*Primary Examiner*—Kriellion Morgan
*Attorney, Agent, or Firm*—Luther A. R. Hall

[57] ABSTRACT

Oligomeric N-hydrocarbyloxy hindered amines are effective light stabilizers in protecting organic substrates against the deleterious effects of actinic light.

21 Claims, No Drawings

OLIGOMERIC N-HYDROCARBYLOXY HINDERED AMINE LIGHT STABILIZERS

This is a continuation-in-part of application Ser. No. 326,703, filed on Mar. 21, 1989, now abandoned.

The instant invention pertains to oligomeric N-hydrocarbyloxy hindered amines and polymer compositions containing said amines which are stabilized against the deleterious effects of actinic light.

BACKGROUND OF THE INVENTION

Monomeric N-hydrocarbyloxy hindered amines are described in copending patent application Ser. No. 259,950, now abandoned.

Copolymers of bis(N-oxylpiperidines) with p-xylylene have been reported in Japanese patent application 79/42000; T. Fujita et al, J. Poly Sci, Poly Chem. Ed, 18, 549 (1980) and 20, 1639 (1982); and J. Poly Sci, Polym Letter Ed, 16, 515 (1978); 17, 353 (1979) and 19, 609 (1981).

The instant oligomeric N-hydrocarbyloxy derivatives prepared from bis-hindered amines and saturated or unsaturated aliphatic hydrocarbons are not described or suggested in the prior art.

DETAILED DISCLOSURE

The instant invention relates to oliqomeric N-hydrocarbyloxy compounds of the formula

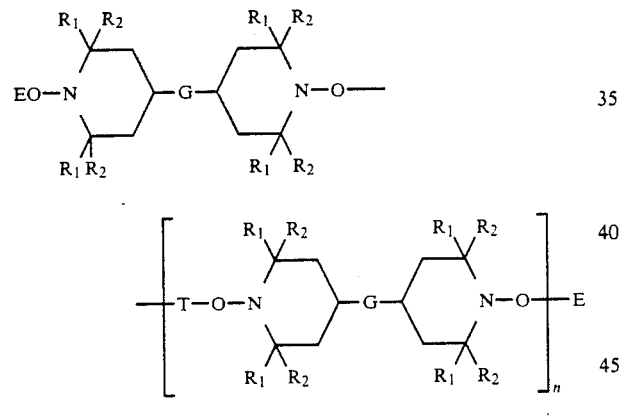

where
n is 1 to 5,
$R_1$ and $R_2$ are independently alkyl of 1 to 4 carbon atoms or $R_1$ and $R_2$ together are pentamethylene,
T is a diradical of an alkane or alkene of 1 to 18 carbon atoms, diradical of a cycloalkane or cycloalkene of 5 to 12 carbon atoms, or a diradical of a saturated or unsaturated bicyclic or tricyclic hydrocarbon of 7 to 12 carbon atoms, with the proviso that the N—O groups are not necessarily attached to the same carbon atom in T,
E is a monovalent radical of an alkane or alkene of 1 to 18 carbon atoms, a monovalent radical of a cycloalkane or cycloalkene of 5 to 12 carbon atoms or a monovalent radical of a saturated or unsaturated bicyclic or tricyclic hydrocarbon of 7 to 12 carbon atoms,
G is an organic linking moiety selected from the group consisting of —OCO—L—COO—, —COO—$L_1$—OCO—, —N$R_3$—CO—L—CON$R_3$—,

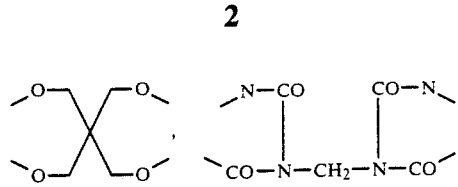

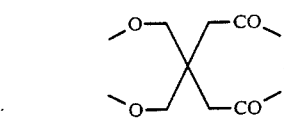

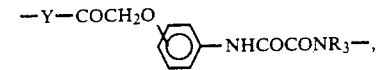

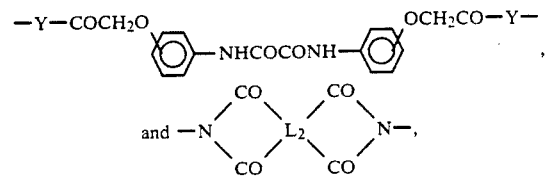

L is a direct bond or a divalent radical of an aliphatic, cycloaliphatic, unsaturated aliphatic or aromatic dicarboxylic acid without the two carboxy groups,
$L_1$ is a divalent radical of an aliphatic, cycloaliphatic or unsaturated aliphatic diol without the two hydroxy groups,
$R_3$ is hydrogen, alkyl of 1 to 8 carbon atoms or

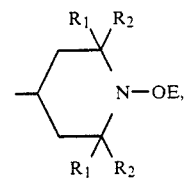

Y is —O— or —N$R_3$—, and
$L_2$ is an aliphatic or aromatic tetravalent radical.
Preferably $R_1$ and $R_2$ are each methyl.
Preferably n is 1 or 2.
Preferably T is a diradical of n-octane, n-heptane or cyclohexane.
Preferably E is octyl, heptyl or cyclohexyl.
Preferably G is —OCO—L—COO— where L is alkylene of 2 to 8 carbon atoms, most preferably 2 or 8 carbon atoms, or phenylene, or
G is —N$R_3$—CO—L—CON$R_3$— where $R_3$ is hydrogen or butyl and L is a direct bond or alkylene of 2 to 8 carbon atoms, most preferably a direct bond or alkylene of 2 or 8 carbon atoms, or
G is

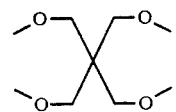

SYNTHESIS

Monomeric N-hydrocarbyloxy derivatives of hindered amines can be made by a variety of synthetic routes. These include:

a. reaction of an N-oxyl compound with an alkyl halide in the presence of tri-n-butyltin hydride (R. L. Kinney et al, J. Am. Chem. Soc. 100, 7902 (1978));

b. reaction of an N-hydroxy compound with an alkyl halide and n-butyllithium or sodium hydride (T. Kurumada et al, J. Poly Sci, Poly Chem. Ed, 22, 277 (1984) and 23, 1477 (1985));

c. The photolysis of a solution of an N-oxyl compound, a hydrocarbon and di-tert-butyl peroxide (D. W. Grattan et al, Polym. Degrad & Stability, 1979, 69);

d. The thermolysis of a solution of an N-oxyl compound, a hydrocarbon and a tert-butyl perester (A. J. Beckwith, J. Org. Chem. 53, 1632 (1988));

e. The photolysis of a solution of an N-oxyl compound, a hydrocarbon and tert-butyl hydroperoxide in an oxygen atmosphere (T. Kurumada et al, J. Polym. Sci, Polym Chem. Ed, 23, 1477 (1985)); and f. The thermolysis of a solution of a hindered amine or an N-oxyl hindered amine, a hydrocarbon, tert-butyl hydroperoxide and a metal oxide catalyst (in copending patent application Ser. Nos. 259,946 and 259,950).

The instant oligomeric N-hydrocarbyloxy hindered amine compounds can be synthesized by appropriate modifications of the methods discussed supra. For example, bis(N-oxyl) compounds can react with hydrocarbon radicals generated from the decomposition of a peroxide or hydroperoxide in the presence of a hydrocarbon solvent with abstractable hydrogen atoms. At sufficiently low concentrations of solvent, two N-oxyl molecules can react with the same solvent molecule, but mixtures of monomeric and oligomeric N-hydrocarbyloxy compounds are nearly always obtained. These mixtures can be easily separated into monomeric and oligomeric N-hydrocarbyloxy compounds by column chromatography.

Bis(N-oxyl) hindered amines can be reacted with tributyltin hydride and aliphatic dihalides, preferably diiodides, to give oligomeric products. Bis(N-hydroxy) hindered ;amines can be alkylated using a suitable base and aliphatic dihalides. These methods are expected to give mixtures of oligomers of different molecular weights. Any terminal halogenated N-hydrocarbyloxy groups can be reduced with tributyltin hydride using standard methodology.

Oligomers having specific molecular weights can be synthesized by preparing difunctional hindered amine intermediates which have one N-hydrocarbyloxy group or bridge and one N-oxyl or N-hydroxy functionality. These intermediates can be coupled using the aliphatic dihalide chemistry discussed in the preceding paragraph.

Although the instant application emphasizes the 2,2,6,6-tetralkylpiperidine structure, it is to be noted that the invention also relates to compounds wherein the following tetraalkyl substituted piperazine or piperazinone moieties are substituted for the above-noted tetraalkylpiperidine moiety:

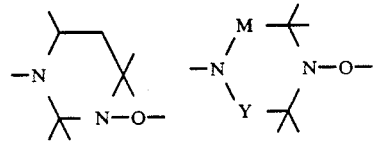

wherein M and Y are independently methylene or carbonyl, preferably M being methylene and Y being carbonyl. It is understood that the identified substituents applicable to such compounds are those which are appropriate for substitution on the ring nitrogen atoms.

Substrates in which the compounds of this invention are particularly useful are polyolefins such as polyethylene and polypropylene; polystyrene, including especially impact polystyrene; ABS resin; elastomers such as e.g. butadiene rubber, EPM, EPDM, SBR and nitrile rubber.

In general polymers which can be stabilized include

1. Polymers of monoolefins and diolefins, for example polyethylene (which optionally can be crosslinked), polypropylene, polyisobutylene, polybutene-1, polymethylpentene-1, polyisoprene or polybutadiene, as well as polymers of cycloolefins, for instance of cyclopentene or norbornene.

2. Mixtures of the polymers mentioned under 1), for example mixtures of polypropylene with polyisobutylene.

3. Copolymers of monoolefins and diolefins with each other or with other vinyl monomers, such as, for example, ethylene/propylene, propylene/butene-1, propylene/isobutylene, ethylene/butene-1, propylene/butadiene, isobutylene/isoprene, ethylene/alkyl acrylates, ethylene/alkyl methacrylates, ethylene/vinyl acetate or ethylene/acrylic acid copolymers and their salts (ionomers) and terpolymers of ethylene with propylene and a diene, such as hexadiene, dicyclopentadiene or ethylidene-norbornene.

4. Polystyrene, poly-(p-methylstyrene).

5. Copolymers of styrene or methylstyrene with dienes or acrylic derivatives, such as, for example, styrene/butadiene, styrene/acrylonitrile, styrene/ethyl methacrylate, styrene/butadiene/ethyl acrylate, styrene/acrylonitrile/methyl acrylate; mixtures of high impact strength from styrene copolymers and another polymer, such as, for example, from a polyacrylate, a diene polymer or an ethylene/propylene/diene terpolymer; and block polymers of styrene, such as, for example, styrene/butadiene/styrene, styrene/isoprene/styrene, styrene/ethylene/butylene/styrene or styrene/ethylene/propylene/styrene.

6. Graft copolymers of styrene, such as, for example, styrene on polybutadiene, styrene and acrylonitrile on polybutadiene, styrene and alkyl acrylates or methacrylates on polybutadiene, styrene and acrylonitrile on ethylene/propylene/diene terpolymers, styrene and acrylonitrile on polyacrylates or polymethacrylates, styrene and acrylonitrile on acrylate/butadiene copolymers, as well as mixtures thereof with the copolymers listed under 5), for instance the copolymer mixtures known as ABS-, MBS-, ASA- or AES-polymers.

7. Halogen-containing polymers, such as polychloroprene, chlorinated rubbers, chlorinated or sulfochlorinated polyethylene, epichlorohydrin homo- and copolymers, polymers from halogen-containing vinyl compounds, as for example, polyvinylchloride, polyvinylidene chloride, polyvinyl fluoride, polyvinylidene fluoride, as well as copolymers thereof, as for example, vinyl chloride/vinylidene chloride, vinyl chloride/vinyl acetate, vinylidene chloride/vinyl acetate copolymers, or vinyl fluoride/vinyl ether copolymers.

8. Polymers which are derived from α,β-unsaturated acids and derivatives thereof, such as polyacrylates and polymethacrylates, polyacrylamide and polyacrylonitrile.

9. Copolymers from the monomers mentioned under (8) with each other or with other unsaturated monomers, such as, for instance, acrylonitrile/butadiene, acrylonitrile/alkyl acrylate, acrylonitrile/alkoxyalkyl acrylate or acrylonitrile/vinyl halogenide copolymers or acrylonitrile/alkyl methacrylate/butadiene terpolymers.

10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinylbutyral, polyallyl phthalate or polyallyl-melamine.

11. Homopolymers and copolymers of cyclic ethers, such as polyalkylene glycols, polyethylene oxide, polypropylene oxide or copolymers thereof with bis-glycidyl ethers.

12. Polyacetals, such as polyoxymethylene and those polyoxymethylenes which contain ethylene oxide as comonomer.

13. Polyphenylene oxides and sulfides, and mixtures of polyphenylene oxides with polystyrene.

14. Polyurethanes which are derived from polyethers, polyesters or polybutadienes with terminal hydroxyl groups on the one side and aliphatic or aromatic polyisocyanates on the other side, as well as precursors thereof (polyisocyanates, polyols or prepolymers).

15. Polyamides and copolyamides which are derived from diamines and dicarboxylic acids and/or from aminocarboxylic acids or the corresponding lactams, such as polyamide 4, polyamide 6, polyamide 6/6, polyamide 6/10, polyamide 11, polyamide 12, poly-2,4,4-trimethylhexamethylene terephthalamide, poly-p-phenylene terephthalamide or poly-m-phenylene isophthalamide, as well as copolymers thereof with polyethers, such as for instance with polyethylene glycol, polypropylene glycol or polytetramethylene glycols.

16. Polyureas, polyimides and polyamide-imides.

17. Polyesters which are derived from dicarboxylic acids and diols and/or from hydroxycarboxylic acids or the corresponding lactones, such as polyethylene terephthalate, polybutylene terephthalate, poly-1,4-dimethylol-cyclohexane terephthalate, poly-[2,2-(4-hydroxyphenyl)-propane] terephthalate and polyhydroxybenzoates as well as block-copolyether-esters derived from polyethers having hydroxyl end groups.

18. Polycarbonates.

19. Polysulfones, polyethersulfones and polyetherketones.

20. Crosslinked polymers which are derived from aldehydes on the one hand and phenols, ureas and melamines on the other hand, such as phenol/formaldehyde resins, urea/formaldehyde resins and melamine/formaldehyde resins.

21. Drying and non-drying alkyd resins.

22. Unsaturated polyester resins which are derived from copolyesters of saturated and unsaturated dicarboxylic acids with polyhydric alcohols and vinyl compounds as crosslinking agents, and also halogen-containing modifications thereof of low flammability.

23. Thermosetting acrylic resins, derived from substituted acrylic esters, such as epoxy-acrylates, urethane-acrylates or silicone-acrylates.

24. Alkyd resins, polyester resins or acrylate resins in admixture with melamine resins, urea resins, polyisocyanates or epoxide resins as crosslinking agents.

25. Crosslinked epoxide resins which are derived from polyepoxides, for example from bis-glycidyl ethers or from cycloaliphatic diepoxides.

26. Natural polymers, such as cellulose, rubber, gelatin and derivatives thereof which are chemically modified in a polymer homologous manner, such as cellulose acetates, cellulose propionates and cellulose butyrates, or the cellulose ethers, such as methyl cellulose.

27. Mixtures of polymers as mentioned above, for example PP/EPDM, Polyamide 6/EPDM or ABS, PVC/EVA, PVC/ABS, PVC/MBS, PC/ABS, PBTP/ABS.

28. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, which materials may be used as plasticizers for polymers or as textile spinning oils, as well as aqueous emulsions of such materials.

29. Aqueous emulsions of natural or synthetic rubber, e.g. natural latex or latices of carboxylated styrene/butadiene copolymers.

30. Polysiloxanes such as the soft, hydrophilic polysiloxanes described, for example, in U.S. Pat. No. 4,259,467; and the hard polyorganosiloxanes described, for example, in U.S. Pat. No. 4,355,147.

31. Polyketimines in combination with unsaturated acrylic polyacetoacetate resins or with unsaturated acrylic resins. The unsaturated acrylic resins include the urethane acrylates, polyether acrylates, vinyl or acryl copolymers with pendant unsaturated groups and the acrylated melamines. The polyketimines are prepared from polyamines and ketones in the presence of an acid catalyst.

32. Radiation curable compositions containing ethylenically unsaturated monomers or oligomers and a polyunsaturated aliphatic oligomer.

33. Epoxymelamine resins such as light-stable epoxy resins crosslinked by an epoxy functional coetherified high solids melamine resin such as LSE 4103 (Monsanto).

In general, the compounds of the present invention are employed in from about 0.01 to about 5% by weight of the stabilized composition, although this will vary with the particular substrate and application. An advantageous range is from about 0.5 to about 2%, and especially 0.1 to about 1%.

The stabilizers of the instant invention may readily be incorporated into the organic polymers by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The resulting stabilized polymer compositions of the invention may optionally also contain various conventional additives, such as the following.

1. Antioxidants 1.1. Alkylated monophenols, for example 2,6-di-tert-butyl-4-methylphenol
2-tert-butyl-4,6-dimethylphenol
2,6-di-tert-butyl-4-ethylphenol
2,6-di-tert-butyl-4-n-butylphenol
2,6-di-tert-butyl-4-i-butylphenol
2,6-di-cyclopentyl-4-methylphenol
2-α-methylcyclohexyl)-4,6-dimethylphenol 2,6-di-octadecyl-4-methylphenol
2,4,6-tri-cyclohexylphenol
2,6-di-tert-butyl-4-methoxymethylphenol 1.2. Alkylated hydroquinones, for example 2,6-di-tert-butyl-4-methoxyphenol
2,5-di-tert-butyl-hydroquinone
2,5-di-tert-amyl-hydroquinone
2,6-diphenyl-4-octadecyloxyphenol 1.3. Hydroxylated thiodiphenyl ethers, for example 2,2'-thio-bis-(6-tert-butyl-4-methylphenol)
2,2'-thio-bis-(4-octylphenol)
4,4'-thio-bis-(6-tert-butyl-3-methylphenol)
4,4'-thio-bis-(6-tert-butyl-2-methylphenol)

1.4. Alkylidene-bisphenols, for example 2,2'-methylene-bis-(6-tert-butyl-4-methylphenol)
2,2'-methylene-bis-(6-tert-butyl-4-ethylphenol)
2,2'-methylene-bis-[4-methyl-6-(α-methylcyclohexyl)-phenol]
2,2'-methylene-bis-(4-methyl-6-cyclohexylphenol)
2,2'-methylene-bis-(6-nonyl-4-methylphenol)
2,2'-methylene-bis-[6-(α-methylbenzyl)-4-nonylphenol]
2,2'-methylene-bis-[6-(α,α-dimethylbenzyl)-4-nonyl-phenol]
2,2'-methylene-bis-(4,6-di-tert-butylphenol)
2,2'-ethylidene-bis-(4,6-di-tert-butylphenol)
2,2'-ethylidene-bis-(6-tert-butyl-4-isobutylphenol)
4,4'-methylene-bis-(2,6-di-tert-butylphenol)
4,4'-methylene-bis-(6-tert-butyl-2-methylphenol)
1,1-bis-(5-tert-butyl-4-hydroxy-2-methylphenyl-butane
2,6-di-(3-tert-butyl-5-methyl-2-hydroxybenzyl)-4-methylphenol
1,1,3-tris-(5-tert-butyl-4-hydroxy-2-methylphenyl)-butane
1,1-bis-(5-tert-butyl-4-hydroxy-2-methylphenyl)-3-n-dodecylmercaptobutane
ethyleneglycol bis-[3,3-bis-(3'-tert-butyl-4'-hydroxyphenyl)-butyrate]
di-(3-tert-butyl-4-hydroxy-5-methylphenyl)-dicyclopentadiene
di-[2-(3'-tert-butyl-2'-hydroxy-5'-methyl-benzyl)-6-tert-butyl-4-methylphenyl] terephthalate.

1.5. Benzyl compounds, for example 1,3,5-tri-(3,5-di-tert-butyl-4-hydroxybenzyl)-2,4,6-trimethylbenzene
di-(3,5-di-tert-butyl-4-hydroxybenzyl) sulfide
3,5-di-tert-butyl-4-hydroxybenzyl-mercapto-acetic acid isooctyl ester
bis-(4-tert-butyl-3-hydroxy-2,6-dimethylbenzyl)dithiol terephthalate
1,3,5-tris-(3,5-di-tert-butyl-4-hydroxybenzyl) isocyanurate
1,3,5-tris-(4-tert-butyl-3-hydroxy-2,6-dimethylbenzyl) isocyanurate
3,5-di-tert-butyl-4-hydroxybenzyl-phosphoric acid dioctadecyl ester
3,5-di-tert-butyl-4-hydroxybenzyl-phosphoric acid monoethyl ester, calcium-salt 1.6. Acylaminophenols, for example 4-hydroxy-lauric acid anilide
4-hydroxy-stearic acid anilide
2,4-bis-octylmercapto-6-(3,5-tert-butyl-4-hydroxyanilino)-s-triazine
octyl-N-(3,5-di-tert-butyl-4-hydroxyphenyl)-carbamate 1.7. Esters of β-(3,5-di-tert-butyl-4-hydroxyphenyl)-propionic acid with monohydric or polyhydric alcohols, for example methanol
diethylene glycol
octadecanol
triethylene glycol
1,6-hexanediol
pentaerythritol
neopentyl glycol
tris-hydroxyethyl isocyanurate
thiodiethylene glycol
di-hydroxyethyl oxalic acid diamide 1.8. Esters of β-(5-tert-butyl-4-hydroxy-3-methylphenyl)-propionic acid with monohydric or polyhydric alcohols, for example methanol
diethylene glycol
octadecanol
triethylene glycol
1,6-hexanediol
pentaerythritol
neopentyl glycol
tris-hydroxyethyl isocyanurate
thiodiethylene glycol
di-hydroxyethyl oxalic acid diamide 1.9 Amides of β-(3,5-di-tert-butyl-4-hydroxyphenyl)-propionic acid for example N,N'-di-(3,5-di-tert-butyl-4-hydroxyphenylpropionyl)-hexamethylenediamine
N,N'-di-(3,5-di-tert-butyl-4-hydroxyphenylpropionyl)-trimethylenediamine
N,N'-di-(3,5-di-tert-butyl-4-hydroxyphenylpropionyl)-hydrazine 2. UV absorbers and light stabilizers 2.1. 2-(2'-Hydroxyphenyl)-benzotriazoles for example, the 5'-methyl-, 3',5'-di-tert-butyl-, 5'-tert-butyl-, 5'-(1,1,3,3-tetramethylbutyl)-, 5-chloro-3',5'-di-tert-butyl-, 5-chloro-3'-tert-butyl-5'-methyl-, 3'-sec-butyl-5'-tert-butyl-, 4'-octoxy, 3',5'-di-tert-amyl-, 3',5'-bis-(α,α-dimethylbenzyl), 3'-tert-butyl-5'-(2-(omega-hydroxyocta-(ethyleneoxy)carbonyl-ethyl)-, 3'-dodecyl-5'-methyl-, and 3'-tert-butyl-5'-(2-octyloxycarbonyl)ethyl-, and dodecylated-5'-methyl derivatives.

2.2. 2-Hydroxy-benzophenones for example, the 4-hydroxy-, 4-methoxy-, 4-octoxy, 4-decyloxy-, 4-dodecyloxy-, 4-benzyloxy-, 4,2',4'-trihydroxy- and 2'-hydroxy-4,4'-dimethoxy derivatives.

2.3. Esters of optionally substituted benzoic acids for example, phenyl salicylate, 4-tert-butylphenyl salicylate, octylphenyl salicylate, dibenzoylresorcinol, bis-(4-tert-butylbenzoyl)-resorcinol, benzoylresorcinol, 3,5-di-tert-butyl-4-hydroxybenzoic acid 2,4-di-tert-butylphenyl ester and 3,5-di-tert-butyl-4-hydroxybenzoic acid hexadecyl ester.

2.4. Acrylates for example, α-cyano-β,β-diphenylacrylic acid ethyl ester or isooctyl ester, α-carbomethoxy-cinnamic acid methyl ester, α-cyano-β-methyl-p-methoxy-cinnamic acid methyl ester or butyl ester, α-carbomethoxy-p-methoxy-cinnamic acid methyl ester, N-(β-carbomethoxy-β-cyanovinyl)-2-methyl-indoline.

2.5. Nickel compounds for example, nickel complexes of 2,2'-thio-bis-[4-(1,1,3,3-tetramethylbutyl)-phenol], such as the 1:1 or 1:2 complex, optionally with additional ligands such as n-butylamine, triethanolamine or N-cyclohexyl-diethanolamine, nickel dibutyldithiocarbamate, nickel salts of 4-hydroxy-3,5-di-tert-butylbenzylphosphonic acid monoalkyl esters, such as of the methyl, ethyl or butyl ester, nickel complexes of ketoximes such as of 2-hydroxy-4-methyl-phenyl undecyl ketoxime, nickel complexes of 1-phenyl-4-lauroyl-5-hydroxy-pyrazole, optionally with additional ligands.

2.6. Sterically hindered amines for example bis-(2,2,6,6-tetramethylpiperidyl) sebacate, bis-(1,2,2,6,6-pentamethylpiperidyl) sebacate, n-butyl-3,5-di-tert.butyl-4-hydroxybenzyl malonic acid bis-(1,2,2,6,6-pentamethylpiperidyl)ester, condensation product of 1-hydroxyethyl-2,2,6,6-tetramethyl-4-hydroxypiperidine and succinic acid, condensation product of N,N'-(2,2,6,6-tetramethylpiperidyl)-hexamethylenediamine and 4-tert-octylamino-2,6-dichloro-s-triazine, tris-(2,2,6,6-tetramethylpiperidyl)-nitrilotriacetate, tetrakis-(2,2,6,6-tetramethyl-4-piperidyl)-1,2,3,4-butanetetracarbonic acid, 1,1'(1,2-ethanediyl)-bis-(3,3,5,5-tetramethylpiperazinone).

2.7. Oxalic acid diamides for example, 4,4'-di-octyloxyoxanilide, 2,2'-di-octyloxy-5,5'-di-tert-butyl-oxanilide, 2,2'-di-dodecyloxy-5,5'-di-tert-butyl-oxanilide, 2-ethoxy-2'-ethyl-oxanilide, N,N'-bis (3-dimethylaminopropyl)-oxalamide, 2-ethoxy-5-tert-butyl-2'-ethyloxanilide and its mixture with 2-ethoxy-2'-ethyl-5,4'-di-tert-butyloxanilide and mixtures of ortho- and para-methoxy-as well as of o- and p-ethoxy-disubstituted oxanilides.

2.8. Hydroxyphenyl-s-triazines for example 2,6-bis-(2,4-dimethylphenyl)-4-(2-hydroxy-4-octyloxyphenyl)-s-triazine; 2,6-bis-(2,4-dimethylphenyl)-4-(2,4-dihydroxyphenyl)-s-triazine; 2,4-bis(2,4-dihydroxyphenyl)-6-(4-chlorophenyl)-s-triazine; 2,4-bis[2-hydroxy-4-(2-hydroxyethoxy)phenyl]-6-(4-chlorophenyl)-s-triazine; 2,4-bis[2-hydroxy-4-(2-hydroxyethoxy)phenyl]-6-phenyl-s-triazine; 2,4-bis[2-hydroxy-4-(2-hydroxyethoxy)phenyl]-6-(2,4-dimethylphenyl)-s-triazine; 2,4-bis[2-hydroxy-4-(2-hydroxyethoxy)phenyl]-6-(4-bromophenyl)-s-triazine; 2,4-bis[2-hydroxy-4-(2-acetoxyethoxy)phenyl]-6-(4-chlorophenyl)-s-triazine, 2,4-bis(2,4- dihydroxyphenyl)-6-(2,4-dimethylphenyl)-s-triazine.

3. Metal deactivators for example, N,N'-diphenyloxalic acid diamide, N-salicylal-N'-salicyloylhydrazine, N,N'-bis-salicyloylhydrazine, N,N'-bis-(3,5-di-tert-butyl-4-hydroxyphenylpropionyl)-hydrazine, 3-salicyloylamino-1,2,4-triazole, bis-benzylidene-oxalic acid dihydrazide.

4. Phosphites and phosphonites for example, triphenyl phosphite, diphenylalkyl phosphites, phenyldialkyl phosphites, tri-(nonylphenyl) phosphite, trilauryl phosphite, trioctadecyl phosphite, di-stearyl-pentaerythritol diphosphite, tris-(2,4-di-tert-butylphenyl) phosphite, di-isodecylpentaerythritol diphosphite, di-(2,4-di-tert-butylphenyl)pentaerythritol diphosphite, tristearylsorbitol triphosphite, tetrakis-(2,4-di-tert-butylphenyl) 4,4'-diphenylylenediphosphonite.

5. Compounds which destroy peroxide, for example, esters of β-thiodipropionic acid, for example the lauryl, stearyl, myristyl or tridecyl esters, mercapto-benzimidazole or the zinc salt of 2-mercaptobenzimidazole, zinc dibutyl-dithiocarbamate, dioctadecyl disulfide, pentaerythritol tetrakis-(β-dodecylmercapto)-propionate.

6. Hydroxylamines for example, N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

7. Polyamide stabilizers for example copper salts in combination with iodides and/or phosphorus compounds and salts of divalent manganese.

8. Basic co-stabilizers for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example Ca stearate, Zn stearate, Mg stearate, Na ricinoleate and K palmitate, antimony pyrocatecholate or zinc pyrocatecholate.

9. Nucleating agents for example, 4-tert-butyl-benzoic acid, adipic acid, diphenylacetic acid.

10. Fillers and reinforcing agents for example, calcium carbonate, silicates, glass fibers, asbestos, talc, kaolin, mica, barium sulfate, metal oxides and hydroxides, carbon black, graphite.

11. Other additives for example, plasticizers, lubricants, emulsifiers, pigments, optical brighteners, flameproofing agents, antistatic agents, blowing agents and thiosynergists such as dilauryl thiodipropionate or distearyl thiodipropionate.

Of particular interest is the utilization of the instant derivatives in a variety of coating systems including ambient cured and acid catalyzed coating systems. In particular, the physical integrity of the coatings is maintained to a higher degree with significant reduction in loss of gloss and yellowing. Key improvements include the substantial absence of the cure retardation encountered with N-alkyl hindered amine light stabilizers; the substantial absence of flocculation and dispersion destabilization seen when N-alkyl hindered amines are utilized in certain pigmented coating systems and the absence of adhesion loss between the coating and polycarbonate substrate. Accordingly, the present invention also relates to the use of the instant compounds, optionally together with further stabilizers, for stabilizing ambient cured coatings based on alkyd resins; thermoplastic acrylic resins; acrylic alkyds; acrylic alkyd or polyester resins optionally modified with silicon, isocyanates, isocyanurates, ketimines or oxazolidines; and epoxide resins crosslinked with carboxylic acids, anhydrides, polyamines or mercaptans; and acrylic and polyester resin systems modified with reactive groups in the backbone thereof and crosslinked with epoxides; against the degradative effects of light, moisture and oxygen.

Furthermore, in their industrial uses, enamels with high solids content based on crosslinkable acrylic, polyester, urethane or alkyd resins are cured with an additional acid catalyst Light stabilizers containing a basic nitrogen group are generally less than satisfactory in this application. Formation of a salt between the acid catalyst and the light stabilizer leads to incompatibility or insolubility and precipitation of the salt and to a reduced level of cure and to reduced light protective action and poor resistance to moisture.

These acid catalyzed stoving lacquers are based on hot crosslinkable acrylic, polyester, polyurethane, polyamide or alkyd resins The acrylic resin lacquers, which can be stabilized against light, moisture and oxygen in accordance with the invention, are the conventional acrylic resin stoving lacquers or thermosetting resins including acrylic/melamine systems which are described, for example, in H Kittel's "Lehrbuch der Lacke und Beschichtungen", Vol. 1 Par 2, on pages 735 and 742 (Berlin 1972), "Lackkunstharze" (1977), by H. Wagner and H. F. Sarx, on pages 229-238, and in S. Paul's "Surface Coatings: Science and Technology" (1985).

The polyester lacquers, which can be against the action of light and moisture, are the conventional stoving lacquers described e.g. in H. and H. F. Sarx, op. cit., on pages 86-99.

The alkyd resin lacquers which can be stabilized against the action of light and moisture in accordance with the invention, are the conventional stoving lacquers which are used in particular for coating automobiles (automobile finishing lacquers), for example lacquers based on alkyd/melamine resins and alkyd/acrylic/melamine resins (see H. Wagner and H. F. Sarx, op. cit., pages 99-123). Other crosslinking agents include glycoluril resins, blocked isocyanates or epoxy resins.

The acid catalyzed stoving lacquers stabilized in accordance with the invention are suitable both for metal finish coatings and solid finishes, especially in the case of retouching finishes, as well as various coil coating applications. The lacquers stabilized in accordance with the invention are preferably applied in the conventional manner by two methods, either by the single-coat method or by the two-coat method. In the latter method, the pigment-containing base coat is applied first and then a covering coat of clear lacquer over it.

It is also to be noted that the instant substituted hindered amines are applicable for use in non-acid catalyzed thermoset resins such as epoxy, epoxy-polyester, vinyl, alkyd, acrylic and polyester resins, optionally modified with silicon, isocyanates or isocyanurates. The epoxy and epoxy-polyester resins are crosslinked with conventional crosslinkers such as acids, acid anhydrides, amines, and the like.

Correspondingly, the epoxide may be utilized as the crosslinking agent for various acrylic or polyester resin systems that have been modified by the presence of reactive groups on the backbone structure.

To attain maximum light stability in such coatings, the concurrent use of other conventional light stabilizers can be advantageous. Examples are the aforementioned UV absorbers of the benzophenone, benzotriazole, acrylic acid derivative, or oxanilide type, or aryl-s-triazines or metal-containing light stabilizers, for example organic nickel compounds. In two-coat systems, these additional light stabilizers can be added to the clear coat and/or the pigmented base coat.

If such combinations are employed, the sum of all light stabilizers is 0.2 to 20% by weight, preferably 0.5 to 5% by weight, based on the film-forming resin.

Examples of different classes of UV absorbers which may be used in the instant compositions in conjunction with the aforementioned piperidine compounds are references in a paper by H. J. Heller in European Polymer Journal Supplement, 1969, pp. 105-132. These classes include the phenyl salicylates, the o-hydroxybenzophenones, the hydroxyxanthones, the benzoxazoles, the benzimidazoles, theoxadiazoles, the triazoles, the pyrimidines, the chinazolines, the s-triazines, the hydroxyphenyl-benzotriazoles, the alpha-cyanoacrylates and the benzoates.

Types of UV absorbers of especial importance are:

(a) 2-(2'-Hydroxyphenyl)-benzotriazoles, for example, the 5'-methyl-, 3',5'-di-tert-butyl-, 5'-tert-butyl-, 5'-(1,1,3,3-tetramethylbutyl)-, 5-chloro-3',5'-di-tert-butyl-, 5-chloro-3'-tert-butyl-5'-methyl-, 3'-sec-butyl-5'-tert-butyl-, 4'-octoxy-, and 3',5'-di-tert-amyl derivatives.

(b) 2-Hydroxy-benzophenones, for example, the 4-hydroxy-, 4-methoxy-, 4-octoxy-, 4-decyloxy-, 4-dodecyl-oxy-, 4-benzyloxy, 4,2',4'-trihydroxy- and 2'-hydroxy-4,4'-dimethoxy derivatives.

(c) Acrylates, for example, alpha-cyano-$\beta,\beta$-diphenyl-acrylic acid ethyl ester or isoctyl ester, alpha-carbomethoxy-cinnamic acid methyl ester, alpha-cyano-$\beta$-methyl-p-methoxy-cinnamic acid methyl ester or butyl ester, alphacarbomethoxy-p-methoxy-cinnamic acid methyl ester, N-($\beta$-carbomethoxy-$\beta$-cyanovinyl)-2-methyl-indoline.

(d) Nickel compounds, for example, nickel complexes of 2,2'-thiobis-[4-(1,1,3,3-tetramethylbutyl)-phenol], such as the 1:1 or 1:2 complex, optionally with additional ligands such as n-butylamine, triethanolamine or N-cyclohexyl-diethanolamine, nickel dibutyldithiocarbamate, nickel salts of 4-hydroxy-3,5-di-tert-butylbenzylphosphonic acid monoalkyl esters, such as of the methyl, ethyl or butyl ester, nickel complexes of ketoximes such as of 2-hydroxy-4-methyl-phenyl undecyl ketonoxime, nickel complexes of 1-phenyl-4-lauroyl-5-hydroxy-pyrazol, optionally with additional ligands.

(e) Oxalic acid diamides, for example, 4,4'-di-octyloxyoxanilide, 2,2'-di-octyloxy-5,5'-di-tert-butyl-oxanilide, 2,2'-di-dodecyloxy-5,5'-di-tert-butyl-oxanilide, 2-ethoxy-2'-ethyl-oxanilide, N,N'-bis-(3-dimethylamino-propyl)-oxalamide, 2-ethoxy-5-tert-butyl-2'-ethyloxanilide and its mixture with 2-ethoxy-2'-ethyl-5,4'-di-tert-butyloxanilide and its mixtures of ortho- and para-methoxy- as well as of o- and p-ethoxy-disubstituted oxanilides.

(f) Hydroxyphenyl-s-triazines such as 2,6-bis(2,4-dimethylphenyl)-4-(2-hydroxy-4-octyloxyphenyl)-s-triazine or the corresponding 4-(2,4-dihydroxyphenyl) derivative.

Of particular value in the instant compositions are the benzotriazoles of high molecular weight and low volatility such as 2-[2-hydroxy-3,5-di(alpha,alpha-dimethyl-benzyl)-phenyl]-2H-benzotriazole, 2-(2-hydroxy-3,5-di-tert-octylphenyl)-2H-benzotriazole, 2-(2-hydroxy-3-alpha,alpha-dimethylbenzyl-5-tert-octyl-phenyl)-2H-benzotriazole, 2-(2-hydroxy-3-tert-octyl-5-alpha,alpha-dimethylbenzylphenyl)-2H-benzotriazole, 2-(2-hydroxy-3,5-di-tert-amylphenyl)-2H-benzotriazole, 2-[2-hydroxy-3-tert-butyl-5-(2-(omega-hydroxy-octa-(ethyleneoxy)carbonyl)-ethylphenyl]-2H-benzotriazole, dodecylated 2-(2-hydroxy-5-methylphenyl)-2H-benzotriazole, 2-[2-hydroxy-3-tert-butyl-5-(2-octyloxycarbonyl)ethylphenyl]-2H-benzotriazole and the 5-chloro compounds corresponding to each of the above named benzotriazoles.

Most preferably the benzotriazoles useful in the instant compositions are 2-[2-hydroxy-3,5-di(alpha,alpha-dimethyl-benzyl)phenyl]-2H-benzotriazole, dodecylated 2-(2-hydroxy-5-methylphenyl)-2H-benzotriazole, 2-[2-hydroxy-3-tert-butyl-5-(2-(omega-hydroxy-octa-(ethyleneoxy) carbonyl)-ethylphenyl]-2H-benzotriazole, 2-[2-hydroxy-3-tert-butyl-5-(2-octyloxycarbonyl)ethylphenyl]-2H-benzotriazole and 5-chloro-2-[2-hydroxy-3-tert-butyl-5-(2-octyloxycarbonyl)ethylphenyl]-2H-benzotriazole.

It is also contemplated that the instant compounds will be particularly effective as stabilizers for polyolefin fibers, especially polypropylene fibers, when used in conjunction with other stabilizers selected from the group consisting of the phenolic antioxidants, hindered amine light stabilizers, organic phosphorus compounds, ultraviolet absorbers and mixtures thereof.

A preferred embodiment of the instant invention pertains to stabilized compositions comprising
(a) an acid catalyzed thermoset coating or enamel based on hot crosslinkable acrylic, polyester or alkyd resins,
(b) a NOE-substituted 2,2,6,6-tetraalkylpiperidine compounds, and
(c) a UV absorber selected from the group consisting of the benzophenones, benzotriazoles, acrylic acid derivatives, organic nickel compounds, aryl-s-triazines and oxanilides.

Further ingredients which the enamels or coatings can contain are antioxidants, for example those of the sterically hindered phenol derivatives, phosphorus compounds, such as phosphites, phosphines or phosphonites, plasticizers, levelling assistants, hardening catalysts, thickeners, dispersants or adhesion promoters.

A further preferred embodiment of the instant invention is a stabilized composition containing components (a), (b) and (c) described above which additionally contains as component (d) a phosphite or phosphonite.

The amount of phosphite or phosphonite (d) which is used in the instant compositions is from 0.05 to 2% by weight, preferably from 0.1 to 1% by weight, based on the film forming resin. In two-coat systems, these stabilizers may be added to the clear coat and/or base coat.

Typical phosphite and phosphonites include triphenyl phosphite, diphenylalkyl phosphites, phenyldialkyl phosphites, tri-(nonylphenyl)phosphite, trilauryl phosphite trioctadecyl phosphite, di-stearyl-pentaerythritol diphosphite, tris-(2,4-di-tert.butylphenyl) phosphite, diisodecylpentaerythritol diphosphite, di-(2,4-di-tert.butylphenyl)pentaerythritol diphosphite, tristearyl-sorbitol triphosphite, tetrakis-(2,4-di-tert butylphenyl)-4,4'-diphenylylenediphosphonite.

The acid catalyzed thermoset enamels must be stabilized in order to function acceptably in end-use applications. The stabilizers used are hindered amines, preferably those substituted on the N-atom by an inert blocking group in order to prevent precipitation of the basic amine stabilized with the acid catalyst with a concomitant retardation in cure, optionally in combination with UV absorbers, such as the benzotriazoles, benzophenones, substituted s-triazines, phenyl benzoates or oxanilides.

The stabilizers are needed to impart greater retention of durability to the cured enamels (as measured by 20° gloss, distinction of image, cracking or chalking); the stabilizers must not retard cure (normal bake for auto finishes at 121° C. and low bake repair at 82° C. (as measured by hardness, adhesion, solvent resistance and humidity resistance), the enamel should not yellow on curing and further color change on exposure to light should be minimized; the stabilizers should be soluble in the organic solvents normally used in coating applications such as methyl amyl ketone, xylene, n-hexyl acetate, alcohol and the like.

The instant hindered amine light stabilizers substituted on the N-atom by an O-substituted moiety fulfill each of these requirements and provide alone or in combination with a UV-absorber outstanding light stabilization protection to the cured acid catalyzed thermoset enamels.

Still another preferred combination of the instant stabilizers is with a hydroxylamine in order to protect polypropylene fibers from gas fading.

The following examples are presented for the purpose of illustration only and are not to be construed to limit the nature or scope of the instant invention in any manner whatsoever.

EXAMPLE 1

Cyclohexanediyl Bis
[(1-cyclohexyloxy-2,2,6,6-tetramethylpiperidin-4-yl)
(1-oxy-2,2,6,6-tetramethylpiperidin-4-yl) sebacate]

A mixture of 20.0 g (41.6 mmol) of di-(2,2,6,6-tetramethylpiperidin-4-yl) sebacate, 43 g (334 mmol) of 70% aqueous t-butyl hydroperoxide, 1.3 g (9.0 mmol) of molybdenum trioxide, and 125 ml of cyclohexane is heated at reflux for 2.3 hours. Water is collected in a Dean-Stark trap. The red reaction mixture is cooled and transferred to a Fischer-Porter bottle. Fresh cyclohexane (25 ml) is used to thoroughly rinse the flask, and the rinsings are added to the pressure bottle. The pressure bottle is immersed in an oil bath (140° C.) for 3 hours whereupon the colorless reaction mixture is cooled to room temperature and filtered. The filtrate is stirred with 10 g of sodium sulfite in 90 ml of water for 2 hours to decompose unreacted hydroperoxide, then diluted with ethyl acetate (200 ml) and water (100 ml). The organic layer is washed with 10% sodium sulfite (100 ml), water (100 ml), saturated sodium chloride (100 ml), then dried over magnesium sulfate and concentrated at reduced pressure. The crude product is purified by flash chromatography (silica gel, 50:1 heptane:ethyl acetate) to afford 17.8 g (63% yield) of a white solid, m.p. 56–9° C., which is di-(1-cyclohexyloxy-2,2,6,6-tetramethyl-piperidin-4-yl) sebacate. The column is then eluted with 10:1 heptane:ethyl acetate to obtain the title compound as a mixture of cyclohexanediyl isomers.

EXAMPLE 2

Heptanediyl
Bis[(1-heptyloxy-2,2,6,6-tetramethylpiperidin-4-yl)
(1-oxy-2,2,6,6-tetramethylpiperidin-4-yl) sebacate]

A mixture of 35.0 g (72.8 mmol) of di-(2,2,6,6-tetramethylpiperidin-4-yl) sebacate, 58.3 (582 mmol) of 90% aqueous t-butyl hydroperoxide, 2.0 g of molybdenum trioxide, and 250 ml of heptane is heated at 140° C. in a Fischer-Porter bottle. The pressure is maintained at 40-50 psi by occasional venting. Heating is discontinued after 7 hours. An additional portion (20.0 g) of 90% t-butyl hydroperoxide is added and the reaction mixture is heated for one hour at 140° C. The reaction is nearly colorless by this time. The reaction mixture is cooled and filtered to remove the catalyst. The organic phase is separated, dried over magnesium sulfate, and concentrated to 100 ml total volume. This solution is passed through silica gel with heptane as the eluent. The filtrate is evaporated to yield 36.9 g (72% yield) of di-(1-heptyloxy-2,2,6,6-tetramethylpiperidin-4-yl) sebacate, a nearly colorless oil. Elution of the column with 10:1 heptane:ethyl acetate then affords the title compound as a mixture of heptanediyl isomers.

EXAMPLE 3

Octanediyl
Bis[(1-octyloxy-2,2,6,6-tetramethylpiperidin-4-yl)
(1-oxy-2,2,6,6-tetramethylpiperidin-4-yl) sebacate]

70% Aqueous t-butyl hydroperoxide (140 g, 1.09 mol) is added over a 6 hour period to a mixture of 75.4 g (0.157 mol) of bis(2,2,6,6-tetramethylpiperidin-4-yl) sebacate, 1.25 g (8.7 mmol) of molybdenum trioxide, and 570 ml of n-octane that has been heated to 115° C. under a nitrogen atmosphere. During the addition, the reaction is maintained at reflux. Water is collected in a Dean-Stark trap. Upon completion of the addition, the red reaction mixture is heated at reflux (95-97° C.) for seven hours to discharge the red color. The molybdenum trioxide is removed by filtration. The yellow filtrate is stirred at ambient temperature for 30 minutes with 15 g of activated charcoal (DARCO) to remove some of the yellow color, and then concentrated at reduced pressure. The crude product is purified by flash chromatography on silica gel (100:3 heptane: ethyl acetate) to afford 92.9 g (80% yield) of di(1-octyloxy-2,2,6,6-tetramethylpiperidin-4-yl) sebacate, a colorless oil. The column is then eluted with 10:1 heptane:ethyl acetate to obtain the title compound as a mixture of octandiyl isomers. The title compound is a colorless oil.

Analysis:
Calcd. for $C_{80}H_{150}N_4O_{12}$: C, 70.7; H, 11.1; N, 4.1.
Found: C, 69.8; H, 11.5; N, 4.1.

EXAMPLE 4

Cyclohexanediyl
Bis[(1-cyclohexyloxy-2,2,6,6-tetramethylpiperidinyl-4-yl) (1-oxy-2,2,6,6-tetramethylpiperidin-4-yl) succinate]

A two-phase mixture of 70% aqueous tert-butyl hydroperoxide (103.9 grams, 807 mmol), cyclohexane (200 ml) and sodium chloride (15 grams) is shaken in a separatory funnel. The organic phase is dried over anhydrous magnesium sulfate, filtered and added to 40 grms (101 mmol) of bis(2,2,6,6-tetramethylpiperidin-4-yl) succinate. Molybdenum trioxide (2.0 grams) is added and the mixture is heated at reflux for one hour. Water is collected in a Dean-Stark trap. The entire reaction mixture is then transferred to a Fischer-Porter pressure bottle and heated for six hours at 140° C. Additional tert-butyl hydroperoxide (90%, 10.1 grams, 101 mmol) is added and heating is resumed for another four hours. The colorless reaction mixture is filtered, concentrated and dissolved in heptane (200 ml). The heptane solution is passed through a column of silica gel with heptane as the eluent to obtrain 41.2 grams (69% yield) of bis(1-cyclohexyloxy-2,2,6,6-tetramethylpiperidin-4-yl) succinate as a white solid melting at 122-126° C. Further elution of the column with 10:1 heptane:ethyl acetate affords the title compound as a mixture of cyclohexanediyl isomers.

EXAMPLE 5

Oligomers of
Bis(1-oxy-2,2,6,6-tetramethylpiperidin-4-yl) Sebacate and Octanediyl When the procedure of Example 3 is repeated using 200 ml of n-octane, a mixture of oligomers containing 2 to 5 bis(1-oxy-2,2,6,6-tetramethylpiperidin-4-yl) sebacate moieties is obtained.

EXAMPLE 6

Oligomers of
Bis(1-oxy-2,2,6,6-tetramethylpiperidin-4-yl) Sebacate and Heptanediyl When the procedure of Example 2 is repeated using 80 ml of heptane, a mixture of oligomers containing 2 to 5 bis(1-oxy-2,2,6,6-tetramethylpiperidin-4-yl) sebacate moieties is obtained.

EXAMPLE 7

Oligomers of
Bis(1-oxy-2,2,6,6-tetramethylpiperidin-4-yl) Sebacate and Cyclohexanediyl When the procedure of Example 1 is repeated using 40 ml of cyclohexane, a mixture of oligomers containing 2 to 5 bis(1-oxy-2,2,6,6-tetramethylpiperidin-4-yl) sebacate moieties is obtained.

EXAMPLE 8

Oligomers of
Bis(1-oxy-2,2,6,6-tetramethylpiperidin-4-yl Succinate and Cyclohexanediyl When the procedure of Example 4 is repeated using 75 ml of cyclohexane, a mixture of oligomers containing 2 to 5 bis(1-oxy-2,2,6,6-tetramethylpiperidin-4-yl) succinate moieties is obtained.

EXAMPLE 9

Cyclohexanediyl
Bis[N,N'-dibutyl-N-(1-cyclohexyloxy-2,2,6,6-tetramethylpiperidin-4-yl)-N'-(1-oxy-2,2,6,6-tetra methyl-piperidin-4-yl)oxamide]

The title compound is prepared by substituting N,N'dibutyl-N,N'-di(2,2,6,6-tetramethylpiperidin-4-yl)oxamide for bis(2,2,6,6-tetramethylpiperidin-4-yl) succinate in the procedure of Example 4.

EXAMPLE 10

Oligomers of Bis[2-((1-oxy-2,2,6,6-tetramethylpiperidin-4-yl)-aminocarbonyl)methoxy]oxanilide and Octanediyl A mixture of oligomers is prepared by substituting bis[2-((2,2,6,6-tetramethylpiperidin-4-yl)aminocarbonyl)methoxy]oxanilide for bis(2,2,6,6-tetramethylpiperidin-4-yl) sebacate in the procedure of Example 5.

EXAMPLE 11

Oligomers of 3,15-Diylbis(oxy)-2,2,4,4,14,14,16,16-octamethyl-7,11,18,21-tetraoxa-3,15-diazatrispiro[5.2.2.5.2]-heneicosane and 1,4-Butanediyl Excess sodium hydride is added to a solution of 100 mmol of 3,15-diyl-bis(hydroxy)-2,2,4,4,14,14,16,16-octamethyl-7,11,18,21-tetraoxa-3,15-diazatrispiro[5.2.2.5.2.2]-heneicosane in tetrahydrofuran. To this solution is added dropwise a solution of 125 mol of 1,4-diiodobutane in tetrahydrofuran. After the alkylation reaction is complete, the reaction mixture is treated with tributyltin hydride and a catalytic amount of 2,2'-azobis(2-methylpropionitrile) to reduce the terminal N-(4-iodobutyloxy) residues.

EXAMPLE 12

Oligomers of Bis(1-oxy-2,2,6,6-tetramethylpiperidin-4-yl) Isophthalate and 1,8-octanediyl Tributyltin hydride (200 mmol) is added dropwise to a solution of 175 mmol of bis(1-oxyl-2,2,6,6-tetramethylpiperidin-4-yl) isophthalate and 100 mmol of 1,8-diiodooctane in chlorobenzene. The crude reaction mixture is passed through a column of silica gel with hexane as the eluent to remove solvent. Further elution with hexane:ethyl acetate affords the product as a mixture of oligomers.

EXAMPLE 13A

1-Octyloxy-2,2,6,6-tetramethylpiperidin-4-yl 1-Oxyl-2,2,6,6-tetramethylpiperidin-4-yl Sebacate Aqueous tert-butyl hydroperoxide (70%, 80.0 grams, 0.621 mol) is added over a five-hour period to a mixture that is preheated to 125° C. of 60.4 grams (0.125 mol) of bis(2,2,6,6-tetramethylpiperidin-4-yl) sebacate, 1.8 grams of molybdenum trioxide and 620 ml of n-octane under a nitrogen atmosphere. During the addition, the reaction mixture is maintained at reflux. Water is collected in a Dean-Stark trap. The red reaction mixture is heated at reflux for two hours after the addition is complete. Solids are removed by filtration, and the red filtrate is concentrated at reduced pressure. The concentrate is purified by flash chromatography on silica gel (20:1, then 10:1 heptane:ethyl acetate) to afford 26.4 grams of the title compound as a red oil.

EXAMPLE 13B 1,8-Octanediylbis[(1-octyloxy-2,2,6,6-tetramethyl-piperidin-4-yl) (1-oxy-2,2,6,6-tetramethylpiperidin-4-yl) sebacate]

A solution of 26.4 grams (42.1 mmol) of the compound formed in Example 13A, 3.6 grams (9.8 mmol) of 1,8-diiodooctane and 50 ml of chlorobenzene is cooled to 10° C. under a nitrogen atmosphere. Tributyltin hydride (7.0 grams, 24.1 mmol) is added dropwise over a 45-minute period to the chilled solution. The reaction mixture is then stirred at room temperature for 16 hours and finally poured onto a column of silica gel. The column is successively eluted with heptane, 100:3 heptane:ethyl acetate, and 50:3 heptane:ethyl acetate. Fractions containing the crude product are combined and evaporated to yield an oil which is washed with aqueous ammonia to remove tributyltin iodide. Final purification by flash chromatography on silica gel (50:3 heptane:ethyl acetate) affords 3.0 grams of the title compound as a colorless oil. FAB/MS: m/z=1359 $(M+H)^+$.

Analysis:
Calcd. for $C_{80}H_{150}N_4O_{12}$: C, 70.7; H, 11.1; N, 4.1.
Found: C, 71.0; H, 11.7; N, 3.9.

EXAMPLE 14A

4-Hydroxy-1-octyloxy-2,2,6,6-tetramethylpiperidine

The title compound is prepared by the dropwise addition of tributyltin hydride to a solution of 4-hydroxy-1-oxyl-2,2,6,6-tetramethylpiperidine and 1-iodooctane in chlorobenzene under a nitrogen atmosphere.

EXAMPLE 14B

1-Octyl-2,2,6,6-tetramethylpiperidin-4-yl 1-Oxyl-2,2,6,6-tetramethylpiperidin-4-yl Isophthalate Isophthaloyl dichloride is added dropwise to a mixture of the compound prepared in Example 14A, 4-hydroxy-1-oxyl-2,2,6,6-tetramethylpiperidine, triethylamine and methylene chloride. The reaction mixture is worked up in the usual manner and purified by flash chromatography on silica gel to afford the title compound.

EXAMPLE 14C 1,8-Octanediylbis[(1-octyloxy-2,2,6,6-tetramethyl-piperidin-4-yl) (1-oxy-2,2,6,6-tetramethylpiperidin-4-yl) isophthalate]

Tributyltin hydride is added to a chlorobenzene solution of 1,8-diiodooctane and the compound prepared in Example 14B. Purification by flash chromatography affords 1-(8-iodooctyloxy)-2,2,6,6-tetramethylpiperidin-4-yl 1-octyloxy-2,2,6,6-tetramethylpiperidin-4-yl isophthalate and the title compound.

The structure of the title compound of Example 14C is seen by reference to the formula A below.

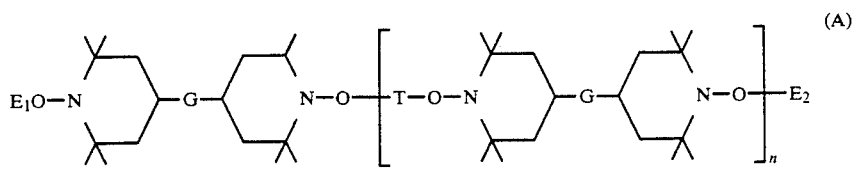

(A)

The title compound has n as 1; G as isophthalate; T as 1,8-octanediyl and $E_1$ and $E_2$ as both octyl.

EXAMPLE 15A (1-[8-(4-Hydroxy-2,2,6,6-tetramethylpiperidin-1-yloxy)]-octyloxy-2,2,6,6-tetramethylpiperidin-4-yl) (1-Octyloxy-2,2,6,6-tetramethylpiperidin-4-yl) Isophthalate The title compound is prepared by the addition of tributyltin hydride to a chlorobenzene solution containing 4-hydroxy-1-oxyl-2,2,6,6-tetramethylpiperidine and 1-(8-iodooctyloxy)2,2,6,6-tetramethylpiperidin-4-yl 1-octyloxy-2,2,6,6-tetramethylpiperidin-4-yl isophthalate isolated in Example 14C.

EXAMPLE 15B

Compound of Formula A where n is 2, G is isophthalate, T is octanediyl and $E_1$ and $E_2$ are each octyl The title compound is prepared by reaction of isophthaloyl dichloride with a mixture of triethylamine, methylene chloride and the compound prepared in Example 15A.

EXAMPLE 16A

1-Methoxy-2,2,6,6-tetramethylpiperidin-4-yl 1-Oxyl-2,2,6,6-tetramethylpiperidin-4-yl Sebacate Sebacoyl chloride is added to a mixture of 4-hydroxy-1-methoxy-2,2,6,6-tetramethylpiperidine, 4-hydroxyl-1-oxyl-2,2,6,6-tetramethylpiperidine, triethylamine and methylene chloride. The reaction mixture is worked up in the usual manner and purified by flash chromatography on silica gel to afford the title compound.

EXAMPLE 16B

Methylenebis(1-methoxy-2,2,6,6-tetramethylpiperidin-4-yl 1-oxo-2,2,6,6-tetramethylpiperidin-4-yl sebacate)

The title compound is prepared by the addition of tributyltin hydride to a chlorobenzene solution of diiodomethane and the compound prepared in Example 16A.

EXAMPLE 17A

Compound of Formula A where n is 1, G is isophthalate, T is octanediyl, $E_1$ is octyl and $E_2$ is oxyl Isophthaloyl dichloride is added to a mixture of 4-hydroxy-1-oxyl-2,2,6,6-tetramethylpiperidine, the compound prepared in Example 15A, triethylamine and methylene chloride. The reaction mixture is worked up in the usual manner and purified by flash chromatography on silica gel to afford the title compound.

EXAMPLE 17B

Compound of Formula A where n is 3, G is isophthalate, T is octanediyl and $E_1$ and $E_2$ are both octyl Tributyltin hydride is added to a chlorobenzene solution of 1,8-diiodooctane and N-oxyl compound prepared in Example 17A. Purification by flash chromatography affords the title compound.

A byproduct isolated from the reaction mixture is the compound of formula A where n is 1, G is isophthalate, T is octanediyl, $E_1$ is octyl and $E_2$ is —$(CH_2)_7CH_2I$.

EXAMPLE 18

Compound of Formula A where n is 4, G is isophthalate, T is octanediyl and $E_1$ and $E_2$ are both octyl The title compound is prepared by the reaction of bis(1-hydroxy-2,2,6,6-tetramethylpiperidin-4-yl) isophthalate with sodium hydride followed by reaction with the byproduct isolated in Example 17B which is the compound of formula A where n is 1, G is isophthalate, T is octanediyl, $E_1$ is octyl and $E_2$ is —$(CH_2)_7CH_2I$.

EXAMPLE 19

Light Stabilization of Polypropylene

This example illustrates the light stabilizing effectiveness of instant stabilizers.

Unstabilized polypropylene powder (Hercules Profax 6501) is thoroughly blended with 0.2% by weight of additive. The blended materials are then milled on a two-roll mill at 182° C. for five minutes, after which time the stabilized polypropylene is sheeted from the mill and allowed to cool. The milled polypropylene is then cut into pieces and compression molded on a hydraulic press at 220° C. and 175 psi ($1.2 \times 10^6$ Pa) into 5 mil (0.127 mm) films. The sample is exposed in a fluorescent sunlight/black light chamber until failure. Failure is taken as the hours required to reach 0.5 carbonyl absorbance by infrared spectroscopy on the exposed films.

Each of the compounds of Examples 1, 2 and 3 are effective as light stabilizers for protecting polypropylene from the deleterious effects of actinic light.

EXAMPLE 20

Stabilization of High Solids Thermoset Acrylic Resin Enamel

A thermoset acrylic enamel based on a binder of 70% by weight of 2-hydroxyethyl acrylate, butyl acrylate, methyl methacrylate, styrene and acrylic acid and of 30% by weight of a melamine resin in the presence of an acid catalyst, p-toluenesulfonic acid, dinonylnaphthalene disulfonic acid or dodecylbenzenesulfonic acid, is formulated to include 2% by weight based on the resin solids of a benzotriazole ultraviolet absorber and an effective stabilizing amount of the test hindered amine light stabilizer.

Commercially available epoxy primed 4"×12" (10.16 cm×30.48 cm) panels (Uniprime from Advanced Coatings Technology) are spray coated with a silver metallic basecoat to a thickness of about 0.8 mil (0.023 mm) and air dried for 3 minutes. The stabilized thermoset acrylic resin enamel is then sprayed onto the basecoated panel to a thickness of about 1.7 mil (0.049 mm). After 15 minutes air-drying, the coated sheets are baked for 30 minutes at 250° F. (121° C.).

After storage for 1 week in a air-conditioned room, the coated panels are subjected to weathering in a QUV exposure apparatus according to test method ASTM G-53/77. In this test, the samples are subjected to weathering in repeated cycles for 4 hours in a humid atmosphere at 50° C. and then for 8 hours under UV light at 70° C. The panels are exposed in the QUV for 1500 hours. The 20° gloss values of the panels are determined before and after exposure.

The loss of gloss of the stabilized panels is considerably less than that of the unstabilized control panels.

What is claimed is:

1. An oligomeric N-hydrocarboxyloxy compound of the formula

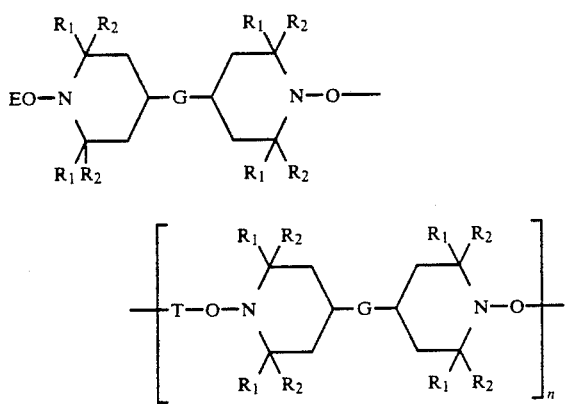

where
n is 1 to 5
$R_1$ and $R_2$ are independently alkyl of 1 to 4 carbon atoms or $R_1$ and $R_2$ together are pentamethylene,
T is a diradical of an alkane or alkene of 1 to 18 carbon atoms, diradical of a cycloalkane or cycloalkene of 5 to 12 carbon atoms, or a diradical of a saturated or unsaturated bicyclic or tricyclic hydrocarbon of 7 to 12 carbon atoms, with the proviso that the N-O groups are not necessarily attached to the same carbon atom in T,
E is a monovalent radical of an alkane or alkene of 1 to 18 carbon atoms, a monovalent radical of a cycloalkane or cycloalkene of 5 to 12 carbon atoms or a monovalent radical of a saturated or unsaturated bicyclic or tricyclic hydrocarbon of 7 to 12 carbon atoms,
G is an organic linking moiety selected from the group consisting of —OCO—L—COO—, —COO—$L_1$—OCO—, —$NR_3$—CO—L—$CONR_3$—,

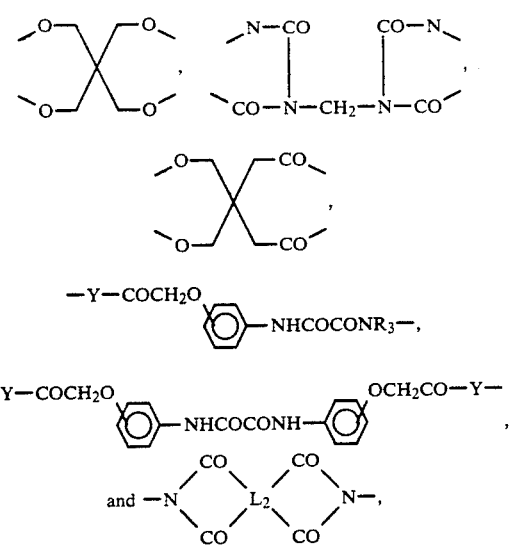

L is a direct bond or a divalent radical of an aliphatic, cycloaliphatic, unsaturated aliphatic or aromatic dicarboxylic acid without the two carboxy groups,
$L_1$ is a divalent radical of an aliphatic, cycloaliphatic or unsaturated aliphatic diol without the two hydroxy groups,
$R_3$ is hydrogen, alkyl of 1 to 8 carbon atoms or

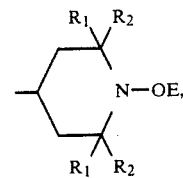

Y is —O— or —$NR_3$—, and
$L_2$ is an aliphatic or aromatic tetravalent radical.

2. A compound according to claim 1 wherein n is 1 to 2.
3. A compound according to claim 1 wherein $R_1$ and $R_2$ are each methyl.
4. A compound according to claim 1 wherein T is a diradical of n-octane, n-heptane or cyclohexane.
5. A compound according to claim 1 wherein E is octyl heptyl or cyclohexyl.
6. A compound according to claim 1 wherein G is —OCO—L—COO— where L is alkylene of 2 to 8 carbon atoms or phenylene.
7. A compound according to claim 6 wherein L is ethylene or octamethylene.
8. A compound according to claim 1 wherein G is —$NR_3$—CO—L—CO—$NR_3$— where $R_3$ is hydrogen or butyl and L is a direct bond or alkylene of 2 to 8 carbon atoms.
9. A compound according to claim 8 wherein L is a direct bond, ethylene or octamethylene.
10. A compound according to claim 1 where G is

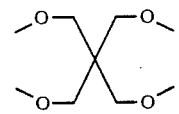

11. A compound according to claim 1 where is cyclohexanediyl bis[(1-cyclohexyloxy-2,2,6,6-tetramethylpiperidin-4-yl) (1-oxy-2,2,6,6-tetramethylpiperidin-4-yl) sebacate].
12. The compound according to claim 1 which is heptanediyl bis[(1-heptyloxy-2,2,6,6-tetramethylpiperidin-4-yl) (1-oxy-2,2,6,6-tetramethylpiperidin-4-yl) sebacate].
13. The compound according to claim 1 which is octanediyl bis[(1-octyloxy-2,2,6,6-tetramethylpiperidin-4-yl) (1-oxy-2,2,6,6-tetramethylpiperidin-4-yl) sebacate].
14. The compound according to claim 1 which is 1,8-octanediyl bis[(1-octyloxy-2,2,6,6-tetramethylpiperidin-4-yl) (1-oxy-2,2,6,6-tetramethylpiperidin-4-yl) sebacate].
15. An organic polymer composition stabilized against deterioration by the adverse effects of actinic light which comprises
   (a) an organic polymer subject to deterioration by the adverse effects of actinic light, and
   (b) an effective stabilizing amount of an oligomeric compound according to claim 1.
16. A composition according to claim 15 wherein the organic polymer is a polyolefin.

17. A composition according to claim 16 wherein the polyolefin is polypropylene.

18. A composition according to claim 15 wherein the oligomeric compound is octanediyl bis[(1-octyloxy-2,2,6,6-tetramethylpiperidin-4-yl) (1-oxy-2,2,6,6-tetramethylpiperidin-4-yl) sebacate].

19. A composition according to claim 15 wherein the organic polymer is a coating system based on alkyd, acrylic, acrylic alkyd, polyester, epoxide, urethane, polyamide, vinyl or epoxy-polyester resins.

20. A composition according to claim 15 which contains a UV absorber or additional light stabilizer.

21. A method for stabilizing an synthetic polymer against oxidative, thermal or actinic degradation which comprises incorporating into said synthetic polymer an effective stabilizing amount of a compound according to claim 1.

* * * * *